United States Patent [19]

Potocnjak et al.

[11] Patent Number: 5,219,730
[45] Date of Patent: Jun. 15, 1993

[54] IDIOTYPE-ANTI-IDIOTYPE IMMUNOASSAY

[75] Inventors: Pedro Potocnjak, Bartolo Soto, Chile; Fidel Zavala, New York, N.Y.; Ruth S. Nussenzweig, New York, N.Y.; Victor Nussenzweig, New York, N.Y.

[73] Assignee: New York University, New York, N.Y.

[21] Appl. No.: 319,578

[22] Filed: Mar. 6, 1989

Related U.S. Application Data

[63] Continuation of Ser. No. 129,313, Nov. 16, 1987, abandoned, which is a continuation-in-part of Ser. No. 425,451, Sep. 28, 1982, abandoned.

[51] Int. Cl.$^5$ .................... C12Q 1/00; G01N 33/53
[52] U.S. Cl. .................... 435/7.93; 435/70.21; 435/240.27; 436/518; 436/536; 436/538; 436/548; 530/388.9; 530/389.2
[58] Field of Search .............. 435/7.93, 70.21, 240.27; 530/388.9, 389.2

[56] References Cited

U.S. PATENT DOCUMENTS

| | | | |
|---|---|---|---|
| 3,395,074 | 1/1976 | Rubenstein et al. | 424/1 |
| 3,966,896 | 6/1976 | Glovsky et al. | 435/7 |
| 4,001,583 | 1/1977 | Barrett | 435/7 |
| 4,017,597 | 4/1977 | Reynolds | 435/7 |
| 4,048,298 | 9/1977 | Niswender | 436/500 |
| 4,130,462 | 12/1978 | Rubenstein et al. | 436/537 |
| 4,536,479 | 8/1985 | Vander-Mallie | 435/28 |

FOREIGN PATENT DOCUMENTS 2487983 2/1982 France .

OTHER PUBLICATIONS

Yalow, R. S. et al, *Principles of Competitive Protein--Binding Assays*, Odell, W. D. et al, eds., J. B. Lippincott Co., Philadelphia (1971), pp. 1-24.
Midgley, A. R. et al, Methods in Enzymology, vol. 70, pp. 266-274 (1980).
Trenkner, E. et al, Journal of Experimental Medicine, vol. 142, pp. 1121-1132 (1975).
Sege, K. et al, Proc. Natl. Acad. Sci. USA, vol. 75, pp. 2443-2447 (May 1978).
Schreiber, A. B. et al, Proc. Natl. Acad. Sci. USA, vol. 77, pp. 7385-7389 (Dec. 1980).
Sy, M. et al, Journal of Experimental Medicine, vol. 151, pp. 896-909 (Apr. 1980).
Nisonoff, A. et al, Clinical Immunol. Immunopath, vol. 21, pp. 397-406 (1981).
Sacks, D. L. et al, J. Exper. Medicine, vol. 155, pp. 1108-1119 (Apr. 1982).
Wassermann, N. H. et al, Proc. Natl. Acad. Sci. USA, vol. 79, pp. 4810-4814 (Aug. 1982).
Brient, B. W. et al, Proc. Natl. Acad. Sci. USA, vol. 68, pp. 3136-3139 (Dec. 1971).
Brient, B. W. et al, J. Exper. Medicine, vol. 132, pp. 951-962 (Nov. 1970).

(List continued on next page.)

*Primary Examiner*—Sam Rosen
*Attorney, Agent, or Firm*—Spencer, Frank & Schneider

[57] ABSTRACT

The present invention provides an immunoassay of general applicability. The assay detects an antigen by its inhibition of the reaction between the combining site of two antibodies. One of the antibodies binds antigen, and the second antibody binds to the combining site or idiotype of the first antibody. It is preferable that both the antibody that binds the antigen and the anti-idiotypic antibody are monoclonal antibodies. The assay provides a method for measuring concentrations of single epitopes without requiring purified antigen, and it is particularly useful for measuring the quantity of any nonpurified antigen present in low concentration in a mixture of antigens. The use of monoclonal antibodies as reagents is advantageous in providing an essentially unlimited supply of highly specific and standardized reagents, without the batch-to-batch variation encountered when using conventional polyclonal antibodies. The invention further provides a screening method for isolating the appropriate monoclonal antibodies of anti-idiotypic specificity.

26 Claims, 1 Drawing Sheet

OTHER PUBLICATIONS

Carson, D. et al, Proc. Natl. Acad. Sci. USA, vol. 70, pp. 235–239 (Jan. 1973).
Kohno, Y. et al, J. of Immunology, vol. 128, pp. 1742–1748 (Apr. 1982).
Morahan, G., Aust. J. Exper. Biol. Med. Sci., vol. 60, pp. 369–382 (1982).
Reth, M. et al, European J. Immunology, vol. 9, pp. 1004–1013 (1979).
Rajewsky, K. et al, The Immune System, vol. 2, pp. 1–11, Karger, Basil (1981).
Yoshida, N. et al, Science, vol. 207, pp. 71–73 (Jan. 1980).
Potocnjak, P. et al, J. Exper. Medicine, vol. 151, pp. 1504–1513 (Jun 1980).
Ju et al, Journal of Experimental Medicine, vol. 152, pp. 170–182, (Jul. 1980).
Current Topics in Microbiology and Immunology, vol. 8 *Lymphocyte Hybridomas*, Springer-Verlag (1978), Ruttin et al, pp. 27–36.
Potocnjak et al, Science, vol. 215, pp. 1637–1639 (Mar. 26, 1982).
Potocnjak, P. et al, J. Experimental Medicine, vol. 151, pp. 1504–1513 (Jun. 1980).
Nelles, M. J. et al, J. Experimental Medicine, vol. 154, pp. 1752–1763 (Dec. 1981).
Tegrain, P. et al, European J. of Immunology, vol. 11, pp. 678–685 (1981).
Sanchez, P. et al, Molecular Immunology, vol. 19, No. 7 pp. 885–892 (1982).
Rauch, J. et al., J. of Immunology, vol. 129, No. 1, pp. 236–241 (Jul. 1982).
Eilat, D. et al Proceedings National Academy of Sciences, vol. 79, pp. 3818–3822 (Jun. 1982).
Hurrell, J. G. R. et al, J. Immunological Methods, vol. 45, pp. 249–254 (1981).
Naot, Y. et al, J. Immunological Methods, vol. 43, pp. 333–340 (1981).
Sher, A. et al, J. Immunology, vol. 109 (1), pp. 176–178 (1972).
Nussenzweig, R. S. et al, Federation Proceedings, vol. 39 (3), p. 805, abstract 2839.
Geha, R. S. et al, J. Immunology, vol. 121 (4), pp. 1518–1523 (Oct. 1978).
Cerny, J. et al, J. of Immunology, vol. 128 (4), pp. 1885–1891 (Apr. 1982).
Gailani, A. et al, J. National Cancer Institute, vol. 58(6), pp. 1553–1555.
Gheuens, J. et al, Eur. J. Immunology, vol. 12, pp. 701–703 (Aug. 1982).
Gheuens, J. et al, J. of Immunological Methods, vol. 47, pp. 183–189 (1981).
Hatzubai, A. et al, J. of Immnuology, vol. 126(6), pp. 2397–2402 (Jun. 1981).
King, M. A. et al, Clin. Exp. Immunol., vol. 45, pp. 544–551 (1981).
Mahoney, J. et al, J. Immunology, vol. 126(1), pp. 113–117 (Jan. 1981).
Marshak-Rothstein, A. et al, Eur. J. of Immunology, vol. 11, pp. 565–572 (1981).
Mitchell, G. F. et al, Aust. J. Exp. Biol. Med. Sci, pt 1, vol. 61, pp. 27–36 (Feb. 1983). Not Prior Art.
Mitchell, G. F. et al, A.J.E.B.A.K., pt 3, pp. 287–302 (1979).
Croce, C.; Banbury Report 10–Patenting of Life Forms, pp. 27–35, Hybridomas in Cancer Research (1982).
Di Felice et al., "A Highly Sensitive Enzyme-Linked Immunosorbent Assay for Idiotype-Bearing Antibodies" Journal of Immunological Methods, 69 (1984) 51–59.
Klein, J.; Immunology The Science of Self-Nonself Discrimination; pp. 205–206; 1982.
Gaulton, G. et al, Ann. Rev. Immunol. 4, pp. 253–257 (1986).
Kearney, J.; Idiotypic Networks, pp. 663–673 (1989).
Ada, G. L.; Fundamental Immunology 2nd Ed; Vaccines, p. 1014 (1989).
Nelles, M. J. Methods in Enzymology, 178, 171–179 (1989).
Katz et al; J. Allergy Clin. Immunol. 76, pp. 255–258 (1985).
Thompson, R. E. et al; Clincal Chemistry, 31, pp. 1833–1837 (1985).
Grzych, J. et al; Methods in Enzymology, 178, pp. 390–405 (1989).
Sluis et al., J. Immunol. Methods, vol. 76, pp. 255–261 (1985).
Morahan, G., J. of Immunol. Methods, 57, 165–170 (1983).
Guillet, et al, J. of Immunol. Methods, 74, 163–171 (1984).
"Inhibition of Idiotype-Anti-Idiotype Interaction for Detection of a Parasite Antigen: A New Immunoassay," by Pedro Potocnjak, Fidel Zavala, Ruth Nussenzweig, and Victor Nussenzweig, *Science*, vol. 215, pp. 1937–1939 (1982).

IDIOTYPE-ANTI-IDIOTYPE IMMUNOASSAY

This application is a continuation of application Ser. No. 07/129,313, filed Nov. 16, 1987, which is a continuation of Ser. No. 06/425,451, filed Sept. 28, 1982, both now abandoned.

BACKGROUND OF THE INVENTION

Known immunoassays include, for example, both the classical radio-immunoassay in which the antigen is labelled and the immunoradiometric assay in which labelled antibodies are used. The principles that govern the competitive binding of ligands to specific receptors are pertinent to the classical radio-immunoassay. The antibody, produced in response to an antigen, serves as the receptor. The ligand in the test sample competes with a constant amount of labelled ligand (i.e. the antigen or suitable derivative) for a limited number of combining sites on the antibody molecules. After equilibration, free labelled antigen is separated from antibody-bound labelled antigen and the radio-activity present in the free or bound state is measured. The extent of the competition between the labelled and unlabelled ligand for the antibody is compared to the inhibitory effectiveness observed with known concentrations of standards. A different type of immunoassay is the immunoradiometric assay (IRMA), based on the use of labelled specific antibodies. In an assay, standards or unknown samples are incubated with an excess of labelled antibody and, after equilibrium has been attained, the unused labelled antibody is removed and the bound fraction counted. In addition to conventional IRMA, "sandwich" techniques have been developed for the assay or large molecules with more than one antigenic determinant. In this case, the standard or sample is first incubated with an excess of antibody bound to an insoluble support and directed against one antigenic determinant. After careful washing, excess of a second, labelled antibody directed against another part of the molecule is added. After incubation and further washes, the counts present in the bound fraction can be determined and will be related directly to the amount of antigen added.

Descriptions of most conventional immunoassays may be found in Langan J. and Clapp J. 1981, *Ligand Assay* (Masson Publishing USA.); and in *Methods in Enzymology*, Vol. 70, part A, 1980 (Academic Press). Abbreviations used throughout are defined as follows:

IRMA = immunoradiometric assay
MC = monoclonal antibody
anti-IdAb = anti-idiotypic antibody
Ag = antigen or component to be determined
Ab1 = antibody specific for Ag = first antibody = antibody 1
Ab2 = antibody specific for the idiotype of Ab1 = antibody 2
BSA = bovine serum albumin
Pb44 = 44,000 dalton membrane protein fragment of *Plasmodium berghei* sporozites
2D12 = a monoclonal anti-idiotypic antibody
3D11 = a monoclonal antibody specific for Pb44
Ag = antigen or component to be determined
MC1 = monoclonal antibody of Ab1 specificity
MC2 = monoclonal antibody of Ab2 specificity
Ab-Ab complexes = complexes of antibody bound to antibody
MCIn = monoclonal antibody specific for insulin
KLH = Keyhole limpet hemocyanin
PBS = phosphate buffered saline The present inventors have discovered a new immunoassay, which differs in one essential aspect from all other previously described immunoassays. The sensitivity and specificity of the classical radioimmunoassay or of IRMA depend primarily on the affinity of one antibody for an antigen. The present invention is based on two specific reactions which take place at or close to the antigen-combining site of one antibody and on the inhibiting effects that they have on each other. In the present invention, Ab1 binds antigen and Ab2 binds Ab1; that is two ligands can bind to Ab1, the antigen and Ab2. If Ab2 is labelled, the inhibitory effect of Ag on the reaction between Ab2 and Ab1 can be measured. It will be understood that the term antigen includes any substance to which an antibody can bind, specifically, including a hapten. The term assay includes both quantitative and qualitative tests.

The novel use of anti-IdAb in an immunoassay provides the following advantages: the assay can measure a single epitope on the antigen, and purification of the antigen is not required. No known immunoassay appears to combine these advantages. Furthermore, it is also convenient to measure, with the immunoassay of this invention, antibodies of a particular antigenic specificity and a particular idiotype.

The present invention is exemplified by the measurement of Pb44, a 44,000 dalton membrane protein found in the sporozites of *Plasmodium berghei*, a rodent malarial parasite. As such, the immunoassay of the present invention has the promise of providing a means of surveying and monitoring the infectivity of mosquito populations. It will be understood that the immunoassay of this invention can be applied to virtually any antigen, including proteins from Plasmodium species infective to humans, and other clinically significant antigens related to viral or bacterial infections, hormonal and enzymatic abnormalities and the like.

The present invention is exemplified by the isolation and cloning of a monoclonal anti-idiotypic antibody (2D12) specific for an idiotype of a monoclonal antibody (3D11) which specifically binds the Pb44 sporozoite surface antigen.

The isolation and characterization of Pb44 was described in U.S. application Ser. No. 234,096, filed Feb. 12, 1981, now U.S. Pat. No. 4,466,917. The isolation of the anti-idiotypic antibody, 2D12, was described by Potocnjak, P. et al., *Science* 215, 1637 (1982). A critical feature of the 2D12 anti-idiotypic antibody is its ability to compete with Pb44 for binding to the anti Pb44 antibody, 3D11. In the present invention, anti-idiotypic antibody can be used either to indirectly measure antigen or to directly measure antibody of a given idiotype. It may also be used for standardizing and monitoring vaccine preparations. It will be understood that the antibodies disclosed herein may be derived from any vertebrate species possessing an immune system, including humans, and such antibodies, including human antibodies, can be used in the immunoassays of the present invention.

Finally, the present invention pertains to a new method of screening monoclonal antibodies having anti-idiotypic specificity and having the capacity to compete with the antigen for binding to the idiotype. The immunoassay of this invention is applicable to the screening of protein fragments useful for developing synthetic or non-synthetic vaccines against malaria, or for vaccines against other diseases. In addition, the sensitivity of the immunoassay is sufficient to allow epidemiological surveys in the investigation of malaria and other vector-transmitted diseases, e.g. in the order of as few as 100 sporozites of P. berghei are readily detectable.

BRIEF DESCRIPTION OF THE INVENTION

The present invention provides an immunoradiometric assay of general applicability. The assay detects an antigen by its inhibition of the reaction between the idiotypes of two antibodies, one which binds antigen, and the second directed against the combining site of the first antibody. It is preferable that both the antibody that binds the antigen (Ab1) and the anti-idiotypic antibody (Ab2) are monoclonal antibodies. The assay provides a method for measuring concentrations of single epitopes without requiring purified antigen, and it is particularly useful for measuring the quantity of any unpurified antigen having a substantially low concentration in a complex mixture of molecules. When monoclonal antibodies are used as reagents, they can be provided in unlimited amounts and in continuous supply. The invention further provides a screening method for isolating the appropriate monoclonal antibodies of anti-idiotypic specificity.

DETAILED DESCRIPTION OF THE INVENTION

Figure 1:
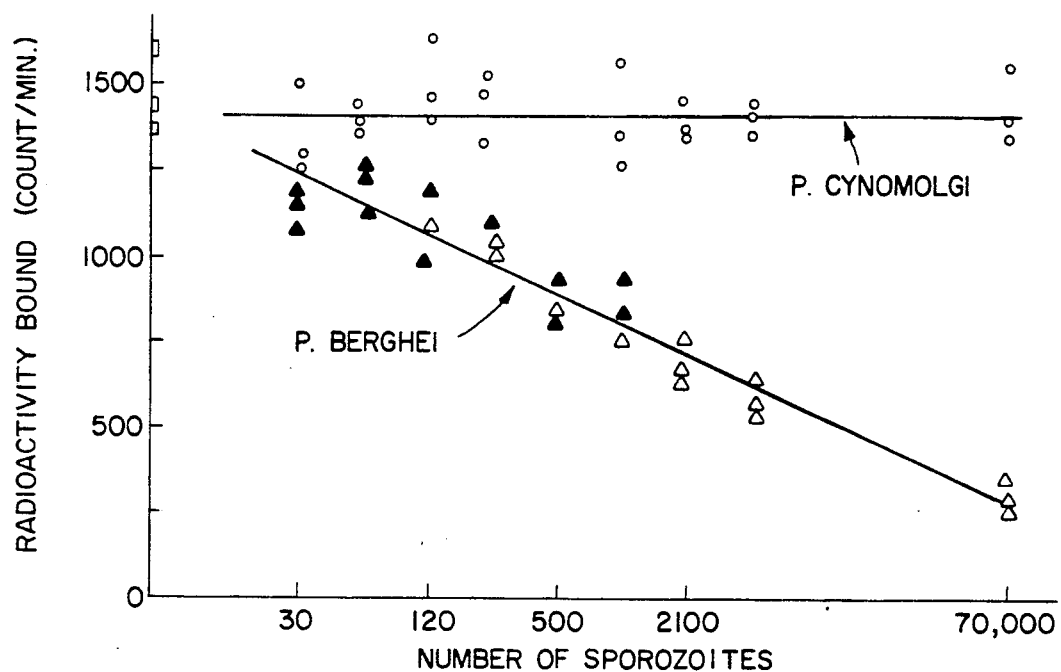

The immunoassay of this invention encompasses three types of reagents: a first antibody (Ab1) which binds Ag (equation 1), and a second antibody (Ab2) capable of binding under certain conditions the first antibody (equation 2). Binding of Ab2 to Ab1 is inhibited by the addition of the relevant antigen, (equations 3 and 4), 1) $Ag + Ab1 \rightarrow Ag - Ab1$
2) $Ab1 + Ab2 \rightarrow Ab1 - Ab2$
3) $Ab1 - Ab2 + Ag \rightarrow Ab1 - Ag + Ab2$
4) $Ag - Ab1 + Ab2 \rightarrow Ab1 - Ab2 + Ag$ An increase in the amount of antigen bound to the first antibody decreases the amount of second antibody that can bind to the first antibody, and the amount of the decrease will depend, inter alia, on the binding constants of Ab1 to Ag and of Ab1 to Ab2, respectively, as well as the respective concentrations of each of the three components. In other words, the two ligands Ab2 and Ag are competitors for the same binding partners, Ab1.

Although the Ag and Ab2 are considered most likely to compete by binding at the same, or overlapping sites on Ab1, the scope of the invention is not so limited. Even if the combining sites for Ab2 and Ag are non-overlapping, the Ab2 may be functional in the present assay provided the binding of either Ab2 or Ag inhibits the binding of the other to Ab1. For general discussion on the immunology of antibody combining sites and of idiotypes, see for example Kabat, E. A. *Structural Concepts in Immunology and Immunochemistry*, Holt 1976, pp. 237-239, 326-335; and Hopper, J. E. et al. *Adv. Immunol.* 13, 57 (1971).

In the preferred immunoassay, excess of insolubilized first antibody is incubated with the antigen present in unknown quantity to be measured. The mixture is then incubated with soluble, labeled second antibody and the solid and liquid phases, are separated. The amount of label in either the solid phase or the liquid phase is measured and the amount of antigen initially present is computed. Another variation on the immunoassay is to label the first antibody, insolubilize the second antibody, incubate the tagged first antibody with the antigen, add insoluble second antibody, separate the solid from liquid phases, and determinate the amount of label in either the solid phase or the liquid phase.

However, it is not necessary to use a solid phase, provided that there is a means to separate bound from unbound labeled antibody, e.g. by sucrose gradients, gel electrophoresis in non-denaturing buffers, double antibody or precipitation with protein A. The requirements for such separations are different from the requirements for separating antibody from non-proteinaceous antigens. The particular requirements in this invention are the separation of a complex of an antibody bound to another antibody (Ab1-Ab2) from either antibody or antibody bound to antigen. A preferred way to separate is to insolubilize either Ab1 or Ab2 by covalent or non-covalent attachment to a solid phase material. Otherwise, tedious and difficult separations based on molecular weight differences may be necessary, e.g. molecular exclusion chromatography with a dextran of Sephadex series. It may also be feasible to use a secondary ligand in solid phase, also known as a solid-phase immunoadsorbent, e.g. protein A or double antibody, such that the ligand binds to one of either Ab1 or Ab2, but not to both Ab1 and Ab2. A disadvantage of a solid-phase immunoadsorbent in that anti-idiotypic antibodies are generally of the same species, if not the same isotype and allotype, as the first antibody. Care must be exercised therefore, to provide appropriate controls to demonstrate that the immunoadsorbent binds only to one of either Ab1 or Ab2, but not to both Ab1 and Ab2. For a general discussion on physicochemical methods of separating bound from the antigen, see, for example, Weir, D. M. (ed.) *Handbook of Experimental Immunology* 2d Ed. Davis 1973, pp. 17.10-17.18. For preparation of some immunoadsorbents, e.g.,the covalent coupling of antibodies to water-insoluble polymers, is represented by reports such as Campbell, D. H. et al. *Proc. Nat. Acad. Sci.* 37, 575 (1951); Weliky, N. et al. *Immunochemistry* 2, 293 (1965); and Weetall, H. H. (ed.) *Immobilized Enzymes, Antigens, Antibodies, and Peptides*, Marcel Dekker, New York, 1975, pp. 513-530.

A preferred embodiment of this invention is to use monoclonal type antibodies for either of antibody 1 or antibody 2, most preferably for both antibody 1 and antibody 2. Monoclonal antibodies (MC) provide homogeneous populations of antibodies in unlimited supply.

The present invention uses hybridoma cell lines to produce the monoclonal antibodies. Hybridoma cells can be produced by the artificial fusion of plasmacytoma cells of mouse origin with spleen cells of immunized mice or rats. The techniques for producing hybridoma cells were first described by Kohler, G., et al, *Nature*, 256, 495 (1975). Clones of hybridoma cells (arising from a single parent plasmacytoma spleen fusion cell) are tested for their ability to produce the desired antibody. The selected clones are maintained in continuous culture. As each clone produces only one antibody having uniform amino acid sequences, the antibodies produced thereby are termed monoclonal. Monoclonal antibodies may be prepared from supernatants of cultured hybridoma cells or from ascites induced by intraperitoneal inoculation of hybrid cells into mice. The latter method is preferred since large amounts of antibody may be made.

Different strategies have been successfully developed to obtain monoclonal antibodies against minor antigenic components of biological fluids or of cell membranes such as Pb44. The special problem in the development of the immunoassay of the present invention was generating a monoclonal antibody with anti-idiotypic specificity. The variety of methods presently available include those described in Legrain, P. et al *Eur. J. Immunol. II*, 678 (1981); Kelsoe, G. et al *Immunol. Rev.* 52, 75 (1980); Nelles, M. J. et al *J. Exp. Med.* 154, 1752 (1981); and Potocnjak, P. et al. *Science* 215, 1637 (1982).

The preferred method in the present invention for obtaining anti-idiotypic antibodies of the monoclonal type involves an immunization procedure with keyhole limpet hemocyanin (KLH) and a screening procedure wherein supernatants of hybridomas are assayed for binding $^{125}$I-labeled monoclonal idiotype. This screening procedure is preferred because it requires an increase in counts bound to identify a clone, unlike another procedure of the present inventors as described in Potocnjak, P. et al. supra, 1982.

The preferred immunization procedure for preparing plasmacytoma cells secreting anti-idiotypic antibodies is as follows. Mice, preferably of the same strain which originated the first antibody, are generally used as recipients. Antibody 1 is polymerized with a highly immunogenic carrier e.g. keyhole limpet hemocyanin (KLH), by mixing the two proteins, each at a concentration of about 5 milligrams/milliliter, in the presence of about 1% glutaraldehyde. After about 60 minutes at room temperature, the mixture is pelleted by centrifugation at high speed, e.g. about 100,000 xg for about 30 minutes. The pellet is resuspended in isotonic buffer or saline, and between about 0.1 milligrams and 0.5 milligrams is injected intravenously into each mouse. It will be understood that the immunogen preparation and the immunization protocol can vary according to classical principles of immunochemistry. For example, it is unnecessary, although preferable, to use mice of the same strain that originated the first antibody. In other words, monoclonal antibody can originate in mice of a different allotype, or even in another animal species, e.g. rats or humans.

The preferred method for screening anti-idiotypic antibodies of the monoclonal type involves a procedure wherein supernatants of hybridoma cells are assayed for binding $^{125}$I-labeled monoclonal idiotype. This procedure is preferably carried out in solid-phase, most preferably on plastic plates. Wells are coated with affinity-purified double antibody, e.g. rabbit antibodies to mouse immunoglobulin at a concentration of between about 10 microgram/milliliter. The wells are washed with buffer containing carrier protein, for example phosphate buffered saline in about 1% bovine serum albumin (PBS-BSA). A volume of hybridoma supernatant is added to each well and incubated at least 2 hours at room temperature, or 12-18 hours at 4° C. The unbound material is washed with e.g. PBS-BSA. At this point it is recommended that any excess sites of the solid-phase double antibody be blocked or saturated by normal antiserum, for example normal mouse Ig if the double antibody is rabbit anti-mouse. The wells are therefore incubated with normal mouse serum diluted 1/40 for at least 1 hour at room temperature. The wells are washed again with e.g. PBS-BSA. Then, finally, about $10^5$ counts of $^{125}$I-labeled antibody 1 diluted in normal mouse serum 1/40 is added to each well. The specific activity should be in the order of $3 \times 10^7$ counts per minute per microgram. Incubation proceeds about 1.5 hours at room temperature. Then the wells are washed with e.g. PBS-BSA and the individual wells counted.

Supernatants having a high number of counts bound occur with an approximate frequency of about 1/250 and about 1/2,500. The cells from these supernatants are expanded and cloned by limiting dilution. The resulting hybridoma is injected intraperitoneally into pristane-treated mice to obtain ascites fluid. Monoclonal antibody can be found in this fluid. The antibody should be tested for inhibition by antigen, preferably by the immunoassay of the present invention. If there is inhibition, then the monoclonal antibody has the desired properties, that is, a specificity for the idiotype of antibody 1 such that binding to antibody 1 is antigen inhibitable.

When monoclonal antibody 2 originates from a different strain or species, the screening procedure as described will usually yield a large number of false positives, most of which are monoclonal antibodies specific for the Fc region of MCI. To avoid the necessity of testing all of the cells corresponding to the false positives for antigen inhibition, it is recommended that the screening procedure be modified to substitute $^{125}$I-labeled antibody 1 with $^{125}$I-labeled Fab fragment of antibody 1. Preparation of Fab fragments is well known in the immunology arts.

While the immunoassay is designed to detect antigens in extremely low concentrations in biological fluids and in biological extracts, the immunoassay of this invention is also adapted for use with more concentrated antigens. Furthermore, virtually any antigen is measurable by the present immunoassay. Pb44, one of the membrane proteins of the *P. berghei* sporozoite, is merely an illustrative example of the antigens measurable. Other antigens include, but are not limited to, ACTH, Aldosterone, Androstenedione, Angiotensin I, Angiotensin II, CEA, Corticosterone, Cortisol, Cortisone, Cyclic AMP, Cyclic GMP, Deoxycorticosterone, Deoxycortisol, DHEA, Dihydrotestosterone, Digitoxin, Digoxin, Estradiol-17B, Estriol, Estrone, Fibrinopeptide A, Gastrin, HAA, Hepatitis B Antigen, HCG, HFSH, HGH, HLH, HPL, HTSH, IgE, Immunoglobulins (IgG, IgA, IgM, IgD, IgE, IgG subgroups, Bence Jones proteins), Insulin, the antigens for Lupus erythematosus, Morphine, Ouabain, Progesterone, Prostaglandin, Testosterone, Thyroxine (T4), and Triiodothyronine (T3).

A wide variety of labels may be attached to the appropriate antibody in the immunoassay of this invention. Isotopes are preferable as labels because of the ease of laboratory use, their reproducibility and commercial availability. Isotopes of choice include, but are not limited to, $^{14}$C, $^{3}$H, $^{131}$I, most preferably $^{125}$I. Other types of labels include enzymes in enzyme immunoassays, e.g. lactic dehydrogenases or beta-galactosidases, fluorescent groups, e.g. rhodamine or fluorescamine, or chemiluminescent groups, e.g. luminol or isoluminol. For reviews of the various kinds or types of labels useful in immunoassays, see, for example, Miller, J. N. *Nature* 295, xxxi, 28 January 1982; Weir, D. M. (ed.), supra, 1973, pp. 17.1-17.9: and Williams, C. A. et al (eds.) *Methods of Immunology and Immunochemistry* Academic Press, Vol.I (1967) and Vol. III (1971), *Methods in Enzymology*, Vol. 74 (1981), Academic Press.

EXAMPLE 1

Isolation and characterization of monoclonal anti-idiotypic antibody specific for 3D11

A monoclonal antibody 1 (3D11) was produced in BALB/c mice against a 44,000-Dalton membrane protein (Pb44) of *Plasmodium berghei*, sporozites, a rodent malaria parasite, by the method of Potocnjak, P., et al, *J. Exp. Med.*, 151, 1504 (1980). This antibody, of the immunoglobulin IgG1 Kappa chain isotype, injected intravenously into mice protects the animals against infection with sporozites.

The monoclonal antibody 2 (2D12) to antibody 3D11 was obtained by injecting BALB/c mice at various skin sites with 3D11 cross-linked with rabbit IgG by treatment with glutaraldehyde, by the method of Avrameas, S., et al, *Scand. J. Immunol.*, 8 (Supp. 7) (1978). A total of 1 to 2 mg of cross-linked protein was given to each mouse over a period of 10 weeks. The spleen cells of two ahimals were used for fusion with the plasmacytoma cell line SP2 as described by Kohler, G., et al, supra. The supernatants of the cultured cells were screened for an activity which inhibited the reaction between $^{125}$I-labelled 3D11 and a conventional rabbit antiserum to the 3D11 idiotype. This antiserum was prepared by immunizing rabbits with 3D11 incorporated in Freund's adjuvant and absorbing their serum several times with normal BALB/c immunoglobulin immobilized on Sepharose TM 4B beads (Pharmacia, Inc., Uppsala, Sweden).

From a total of 700 wells originating from two fusions, one supernatant was found which contained antibodies having the desired properties. The cells from the positive well were expanded and cloned by limiting dilution. The resulting hybridoma or producing antibody 2 (2D12) was injected intraperitoneally into pristane-treated mice to obtain ascites fluid. The monoclonal antibody 2 (IgG2a, Kappa chain) was present in this fluid at concentrations of 2 to 4 mg/ml.

The effect of the Pb44 antigen on the 3D11/2D12 interaction was evaluated by a solid-phase immunoassay (4i assay). A volume of 50 microliters of 3D11, at a concentration of 50 ug/ml solution in phosphate buffered saline (PBS), was placed into each of the wells of disposable flexible plastic plates and incubated at room temperature for 2-8 hours. The wells were then washed several times with PBS containing 1 percent bovine serum albumin (PBS-BSA) and 25 microliters of a dilution of an extract of *P. berghei* in PBS were added to the wells. The *P. berghei* extract was prepared by disrupting the partially purified parasites in a French pressure cell. After two additional hours of incubation, 10 microliters ($1.5 \times 10^4$ counts per min.) of a solution of $^{125}$I-labeled 2D12 monoclonal antibody (specific activity, $2 \times 10^7$ counts per min. per microgram) in PBS-BSA were added. The incubation then proceeded overnight at 4° C. The plates were washed several times with PBS-BSA and the individual wells counted in a gamma counter. The results are reported in FIG. 1.

FIG. 1 shows that the extracts of *P. berghei* inhibited the 3D11/2D12 reaction in a dose-dependent manner. Significant inhibition was obtained with extracts from as few as 100 sporozites. FIG. 1 also shows by contrast that extracts of *P. cynomolgi* (a simian malarial parasite) had no inhibitory effect.

To demonstrate that the inhibition was due to Pb44, the extracts containing Pb44 were treated with Sepharose TM beads coupled with 3D11. As a control, beads coupled with 2D12 were used. The removal of Pb44 by the specific 3D11 immunoadsorbent reversed the inhibitory effect of the extracts, whereas the 2D12 immunoadsorbent did not.

EXAMPLE 2

Detection of *P. berghei* Sporozoites in single mosquitoes

Figure 2:
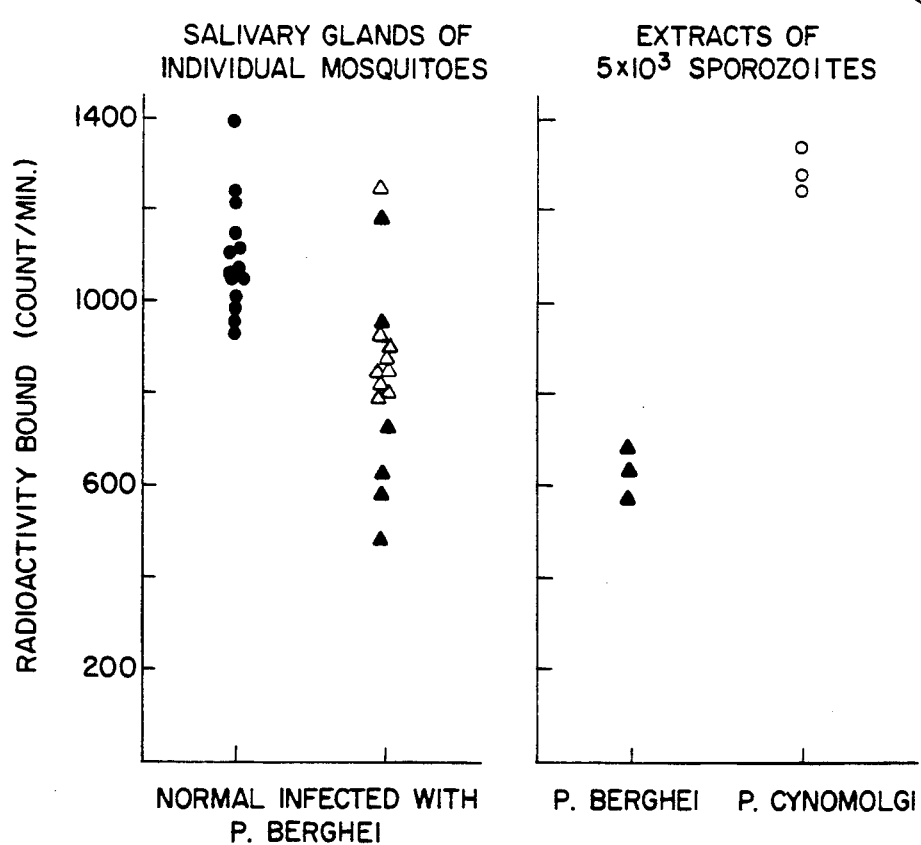

The sensitivity of the 4i assay was determined to be sufficient to detect infection in single mosquitoes, as shown in FIG. 2. Salivary glands were dissected from a population of *Anopheles stephensi* mosquitoes in which 90% were infected with sporozites of *P. berghei*. The salivary glands were extracted individually in 40 microliters of PBS-BSA by freezing and thawing followed by boiling for 5 minutes in water vapors. As a control, salivary glands of normal mosquitoes were subjected to the same treatment. After centrifugation at 8000 g for 2 minutes, the supernatants were assayed for inhibitory activity as described in Example 1, supra. Extracts of partially purified *P. berghei* and *P. cynomolgi* obtained by centrifugation of parasites disrupted in a French pressure cell were used as positive and negative controls, respectively.

EXAMPLE 3

Screening of Wells of Hybridomas for the Presence of Anti-idiotypic Antibodies

The following reactions are carried out in the wells of plastic plates A volume of 50 microliters of affinity-purified rabbit antibodies to mouse immunoglobulin, concentration of 10 micrograms/ml, is added to each well and incubated overnight at 4° C. The wells are then washed with phosphate-buffered saline containing 1% bovine serum albumin (PBS-BSA). A volume of 35 microliters of hybridoma supernatant is next added to the washed and coated wells, and incubation is performed for 4 hours at room temperature. The wells are washed again with PBS-BSA, then each is incubated 1 hr. at room temperature with 50 microliters of normal mouse serum, diluted 1:40 in phosphate-buffered saline. After the wells are washed again with PBS-BSA, a volume of 35 microliters containing $10^5$ counts per minute of $^{125}$I-labeled 3D11 diluted 1/40 in normal mouse serum is added to each well, and incubated 1.5 hours at room temperature. The iodinated 3D11 has a specific activity of about $3 \times 10^7$ counts per minute per microgram of protein. The wells are washed once more with PBS-BSA, then counted individually.

EXAMPLE 4

Enzyme Immunoassay for Insulin with an Insolubilized Antibody 2

A. Preparation of Reagents

A monoclonal antibody specific for insulin (MCIn) is isolated and cloned by the methods and procedures of Kohler, G. et al *Nature* 256, 495 (1975) and Avrameas, S. et al. *Scand. J. Immunol.* 8 (Suppl 7) (1978). The MCIn is then conjugated to *E. coli*. beta-galactosidiase by the method of Kato, K. et al *Eur. J. Biochem.* 62, 285 (1976) to form beta-gal-MCIn. An anti-idiotypic antibody specific for the idiotype of the anti-insulin monoclonal antibody (MCIdIn) is then isolated and cloned by the methods and procedures of Example 1 by substituting 3D11 of Example 1 with the anti-insulin monoclonal antibody of this Example. The MCIdIn is cross-linked to agarose by cyanogen bromide activation according to Cuatrecasas, P. et al *Meth. Enzymol.* 22, 345 (1971) to form MCIdIn-agarose.

B. Protocol for Assay

The B-gal-MCIn is incubated with either unknowns suspected to contain insulin, or standards containing known concentrations of insulin, for a period of 24 hours at 4° C. in 1.5 ml polypropylene microcentrifuge tube. The mixture is then added to an excess of MCIdIn-agarose and incubated 1 hour at 4° C., followed by centrifugation at 10,000 xg for 2 minutes. The supernatant is assayed for residual beta-galactosidase activity by spectrofluorometric detection. Increasing the amount of added antigen increases the amount of beta-galactosidase activity in the supernatant.

EXAMPLE 5

Radioimmunoassay of P. berghei Sporozoites with Polyclonal Anti-Idiotypic Antibody An antiserum specific for the idiotype of 3D11 is obtained by injecting rabbits at various skin sites with insolubilized 3D11, prepared by cross-linking 3D11 with keyhole limpet hemocyanin in the presence of glutaraldehyde according to the method of Avrameas, S. et al *Scand. J. Immunol.*, 8 (Supp. 7) (1978). The antiserum is first absorbed with large excess of agarose-normal mouse serum, and agarose-KLH, then passed over an agarose-3D11 column prepared according to Cuatrecasas, P. et al *Biochemistry* 11, 2291 (1972). The bound material, that is, polyclonal anti-3D11 idiotype, is eluted with excess Pb44 antigen. The eluted antibody will then be separated from the excess Pb44 by chromatographic techniques, or by affinity purification over an agarose-antiPb44 antibody of different specificity than 3D11. This procedure selects from the rabbit anti-3D11 only that fraction of antibody whose binding to 3D11 can be inhibited by antigen. This fraction is the only one that can be used in this invention. The rabbit anti-3D11 idiotype is then labelled to a specific activity of about $10^8$ counts per minute per microgram. The 4i-assay of Example 1 is repeated, but substituting $^{125}$I-2D12 of Example 1 with the polyclonal, $^{125}$-I-labelled rabbit anti-idiotypic antibody of this Example.

EXAMPLE 6

Radioimmunoassay of P. berghei sporozites with Specific Antibody having a Different Idiotype A monoclonal antibody 3 (MC3) against Pb44 of *P. berghei* sporozites is produced by the method Potocnjak, P. et al *J. Exp. Med.*, 151, 1504 (1980), such that it does not react detectably with 2D12 of Example 1, as measured by the interaction of $^{125}$I-2D12 and MC3 coupled to beads. A monoclonal antibody (MC4) specific for the idiotype of MC3 is then cloned and isolated by the procedures and methods of Example 1, except that antibody 3D11 of Example 1 is substituted with MC3 of this Example. The 4i assay of Example 1 is repeated except that antibody 3D11 of Example 1 is substituted with MC3 of this Example and antibody 2D12 of Example 1 is substituted with MC4 of this Example.

EXAMPLE 7

Radioimmunoassay of *P. berghei* sporozites with Polyclonal Antibody Specific for Pb44 and with Polyclonal Anti-Idiotypic Antibody A mouse antiserum specific for Pb44 is affinity-purified on a Pb44-column. The bound and eluted antibody (AbPb44) is then cross-linked with KLH by treatment with glutaraldehyde according to the method of Avrameas, S. et al, supra, 1978, to yield AbPb-KLH. An antiserum specific for the idiotype or idiotypes of AbPb44 is obtained by injecting rabbits at various sites with the AbPb44-KLH, absorbing their serum with excess agarose KLH and agarose-normal mouse serum. The absorbed serum (Id-Ab) is passed on affinity-purified AbPb44 coupled to beads. The Id-Ab will bind to AbPb44. Excess Pb44 will then be passed through the column. From the eluted material, containing a fraction of IdAb and excess Pb44, the Id-Ab will be isolated as specified in example 5. The IdAb is then $^{125}$I-labelled. The 4i assay of Example 1 is repeated, except that antibody 3D11 of Example 1 is substituted with AbPb44 and antibody 2D12 of Example 1 is substituted with IdAb.

It will be understood by those skilled in the art that the present invention, the techniques and principles disclosed herein, are susceptible to modification by those of ordinary skill in the art and that the present invention is intended to include in scope all such modifications, extensions, etc., as come within the scope of ordinary skill.

What is claimed is:

1. A competitive immunoassay method to detect a quantity of an unpurified antigen (Ag) using idiotype-anti-idiotype interaction between a first monoclonal idiotypic antibody (Ab1) and a different second anti-idiotypic monoclonal antibody (Ab2) specific for an idiotype of said first monoclonal idiotypic antibody, whereby Ab2 and Ag compete for Ab1, comprising:

(a) providing a quantity of labeled first monoclonal idiotypic antibody (Ab1) of defined specificity for an antigen and a quantity of said unpurified antigen (Ag), said quantities so selected that they from detectable complexes of labeled first monoclonal idiotypic antibody (Ab1) and said unpurified antigen (Ag);

(b) incubating said quantity of labeled first monoclonal idiotypic antibody (Ab1) and said unpurified antigen (Ag) to form detectable complexes of labeled first monoclonal idiotypic antibody bound to said unpurified antigen,

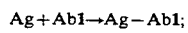

(c) providing a quantity of second monoclonal anti-idiotypic antibody (Ab2), said quantity so selected that said labeled first monoclonal idiotypic antibody (Ab1) and said second monoclonal anti-idiotypic antibody (Ab2) form detectable complexes of said labeled first monoclonal idiotypic antibody (Ab1) and said second monoclonal anti-idiotypic antibody (Ab2) in the presence of said antigen (Ag);

(d) incubating said quantity of second monoclonal anti-idiotypic antibody (Ab2) with said mixture of step (b) to form detectable Ab1-Ab2 complexes,

(e) separating complexes of labeled first monoclonal idiotypic antibody bound to antigen, Ag-Ab1, from said Ab1-Ab2 complexes;

(f) determining the amount of Ab1-Ab2 complexes with said label which provides a detectable signal; and (g) determining the quantity of said antigen (Ag).

2. An immunoassay method according to claim 1 wherein said idiotype of said first monoclonal idiotype antibody, after binding to the antigen, will not bind to said second monoclonal anti-idiotypic antibody.

3. An immunoassay method according to claim 1 or 2, wherein the unlabeled second monoclonal antibody is in the form of a solid-phase immunoabsorbent.

4. An immunoassay method according to claim 3 wherein said label is a radioactive isotope, enzyme, fluorescent group or chemiluminescent group.

5. An immunoassay method according to claim 3 wherein said label is $^{125}$I.

6. An immunoassay method according to claim 3 wherein said antigen is Pb44 of *Plasmodium berghei* sporozites.

7. An immunoassay method according to claim 3, wherein the antigen is selected from the group consisting of adrenocorticotropic hormone (ACTH), aldosterone, androstenedione, Angiotension, I, Angiotension II, carcinoembryonic antigen, Corticosterone, Cortisol, Cortisone, Cyclic guanosine monophosphate, deoxycorticosterone, deoxycortisol, cyclic adenosine monophosphate, digitoxin, digoxin, estradiol-17B, estriol, estrone, fibrinopeptide A, gastrin, hepatitis B antigen, immunoglobulines, insulin, the antigens for Lupus erythematosus, morphine, ouabain, progesterone, prostaglandin, testosterone, thyroxine (T4), triiodothyronine (T3), human growth hormone, chorionic gonadotropin (HCG), human follicle stimulating hormone, human lutiinizing hormone, human prolactin, human thyroid stimulating hormone, and dehydroepiandrosterone.

8. The competitive immunoassay method according to claim 1, wherein said antigen (Ag) is present in a mixture of antigens.

9. A screening method for isolating monoclonal anti-idiotypic antibodies in hybridoma cell culture supernatants using antigen inhibition of idiotype-anti-idiotype interaction between a first monoclonal idiotypic antibody and a different second monoclonal anti-idiotypic antibody, comprising:
(a) coating a solid-phase surface with said first monoclonal idiotypic antibody wherein said first monoclonal idiotypic antibody, after binding to antigen, will not bind to said second monoclonal anti-idiotypic antibody;
(b) washing said surface;
(c) contacting said surface of step (b) with a hybridoma cell culture supernatant suspected to contain said second monoclonal anti-idiotypic antibody;
(d) washing said surface of step (c);
(e) contacting the product of step (d) with normal serum of the same species as said second monoclonal anti-idiotypic antibody;
(f) washing the surface of the product of step (e);
(g) contacting the product of step (f) with said first monoclonal idiotypic antibody labeled to provide a detectable signal;
(h) washing the surface of the product of step (g);
(i) identifying the presence of said labeled first monoclonal idiotypic antibody in supernatants by the presence of said detectable signal; (j) testing the supernatants identified in step (i) for inhibition by an unpurified antigen, of the interaction between said labeled first monoclonal idiotypic antibody and said second unlabeled monoclonal anti-idiotypic antibody according to the method of claim 1; and
(k) selecting hybridomas of the supernatants that show said inhibition for further cloning.

10. The screening method according to claim 9, wherein said antigen is present in step (j) in a mixture of antigens.

11. A method of screening monoclonal antibodies according to claim 9 wherein said species is a mammal.

12. A method of screening monoclonal antibodies according to claim 9 wherein said species is a mouse.

13. A method of screening monoclonal antibodies according to claim 9 wherein said species is a human.

14. A method of screening monoclonal antibodies according to claim 9 wherein said label is $^{125}$I.

15. A method of screening monoclonal antibodies according to claim 9 wherein said antigen is Pb44 of *Plasmodium berghei* sporozites.

16. A method of screening monoclonal antibodies according to claim 9 wherein said solid phase surface is the inside surface of the wells of a plastic microtiter plate.

17. A method of screening monoclonal antibodies according to claim 9, wherein said antibody coated on a solid-phase surface specific for an isotype of said second antibody is affinity purified over an immunoabsorbent of said second antibody prior to being coated on said solid-phase surface.

18. A competitive immunoassay method to detect a quantity of an unpurified Pb44 of Plasmodium berghei sporozites (Pb44) using idiotype-anti-idiotype interaction between a first monoclonal idiotypic antibody (Ab1) and a different second anti-idiotypic monoclonal antibody (Ab2) specific for an idiotype of said first monoclonal idiotypic antibody, whereby Ab2 and Pb44 compete for Ab1, comprising:
(a) providing a quantity of labeled first monoclonal idiotypic antibody (Ab1) of defined specificity for an antigen and a quantity of said unpurified Pb44 of Plasmodium berghei sporozites, said quantities so selected that they form detectable complexes of labeled first monoclonal idiotypic antibody (Ab1) and said unpurified Pb44 of Plasmodium berghei sporozites;
(b) incubating said quantity of labeled first monoclonal idiotypic antibody (Ab1) and said unpurified Pb44 of Plasmodium berghei sporozites to form detectable complexes of labeled first monoclonal idiotypic antibody bound to said unpurified Pb44, Pb44+Ab1→Pb44-Ab1;

(c) providing a quantity of second monoclonal anti-idiotypic antibody (Ab2) in the form of a solid-phase immunoabsorbent, said quantity so selected that said labeled first monoclonal idiotypic antibody (Ab1) and said second monoclonal anti-idiotypic antibody (Ab2) in the form of a solid-phase immunoabsorbent form detectable complexes of said labeled first monoclonal idiotypic antibody (Ab1) and said second monoclonal anti-idiotypic antibody (Ab2) in the form of a solid-phase immunoabsorbent in the presence of said Pb44 of Pasmodium berghei sporozites;
(d) incubating said quantity of second monoclonal anti-idiotypic antibody (Ab2) with said mixture of step (b) to form detectable Ab1-Ab2 complexes, Pb44-Ab1+Ab2→Pb44+Ab1-Ab2;

(e) separating Pb-44-Ab1 complexes of labeled first monoclonal idiotypic antibody bound to Pb44 from said Ab1-Ab2 complexes;
(f) determining the amount of Ab1-Ab2 complexes with said label which provides a detectable signal; and
(g) determining the quantity of said Pb44 of Plasmodium berghei sporozites.

19. A competitive immunoassay method to detect a quantity of an unpurified Pb44 of Plasmodium berghei sporozites (Pb44) using idiotype-anti-idiotype interaction between a first monoclonal idiotypic antibody (Ab1) and a different second anti-idiotypic monoclonal antibody (Ab2) specific for an idiotype of said first monoclonal idiotypic antibody, whereby Ab2 and Pb44 compete for Ab1, comprising:
   (a) providing a quantity of labeled first monoclonal idiotypic antibody (Ab1) of defined specificity for an antigen and a quantity of said unpurified Pb44 of Plasmodium berghei sporozites, said quantities so selected that they form detectable complexes of labeled first monoclonal idiotypic antibody (Ab1) and said unpurified Pb44 of Plasmodium berghei sporozites;
   (b) incubating said quantity of labeled first monoclonal idiotypic antibody (Ab1) and said unpurified Pb44 of Plasmodium berghei sporozites to form detectable complexes of labeled first monoclonal idiotypic antibody bound to said unpurified Pb44, Pb44+Ab1→Pb44-Ab1;

(c) providing a quantity of second monoclonal anti-idiotypic antibody (Ab2) in the form of a solid-phase immunoabsorbent, said quantity so selected that said labeled first monoclonal idiotypic antibody (Ab1) and said second monoclonal anti-idiotypic antibody (Ab2) in the form of a solid-phase immunoabsorbent form detectable complexes of said labeled first monoclonal idiotypic antibody (Ab1) and said second monoclonal anti-idiotypic antibody (Ab2) in the presence of said Pb44 of Plasmodium berghei sporozites, wherein said Pb44 is not bound to said first monoclonal idiotypic antibody (Ab1);
   (d) incubating said quantity of second monoclonal anti-idiotypic antibody (Ab2) with said mixture of step (b) to form detectable Ab1-Ab2 complexes, Pb44-Ab1+Ab2→Pb44+Ab1-Ab2;

(e) separating complexes of labeled first monoclonal idiotypic antibody bound to Pb44, Pb44-Ab1, from said Ab1-Ab2 complexes;
   (f) determining the amount of Ab1-Ab2 complexes with said label which provides a detectable signal; and
   (g) determining the quantity of said Pb44 of Plasmodium berghei sporozites.

20. A competitive immunoassay method to detect a quantity of an unpurified antigen (Ag) using idiotype-anti-idiotype interaction between a first rodent monoclonal idiotypic antibody (Ab1) and a different second rodent monoclonal anti-idiotypic antibody (Ab2) specific for an idiotype of said first rodent monoclonal idiotypic antibody, whereby Ab2 and Ag compete for Ab1, comprising:
   (a) providing a quantity of labeled first rodent monoclonal idiotypic antibody (Ab1) of defined specificity for an antigen and a quantity of said unpurified antigen (Ag), said quantities so selected that they form detectable complexes of labeled first rodent monoclonal idiotypic antibody (Ab1) and said unpurified antigen (Ag);
   (b) incubating said quantity of labeled first rodent monoclonal idiotypic antibody (Ab1) and said unpurified antigen (Ag) to form detectable complexes of labeled first rodent monoclonal idiotypic antibody bound to said unpurified antigen, Ag+Ab1→Ag-Ab1;

(c) providing a quantity of second rodent monoclonal anti-idiotypic antibody (Ab2), said quantity so selected that said labeled first rodent monoclonal idiotypic antibody (Ab1) and said second rodent monoclonal anti-idiotypic antibody (Ab2) form detectable complexes of said labeled first rodent monoclonal idiotypic antibody (Ab1) and said second rodent monoclonal anti-idiotypic antibody (Ab2) in the presence of said antigen (Ag);
   (d) incubating said quantity of second rodent monoclonal anti-idiotypic antibody (Ab2) with said mixture of step (b) to form detectable Ab1-Ab2 complexes, Ag-Ab1+Ab2→Ag+Ab1-Ab2;

(e) separating complexes of labeled first rodent monoclonal idiotypic antibody bound to antigen, Ag-Ab1, from said Ab1-Ab2 complexes;
   (f) determining the amount of Ab1-Ab2 complexes with said label which provides a detectable signal; and
   (g) determining the quantity of said antigen (Ag).

21. A screening method for isolating rodent monoclonal anti-idiotypic antibodies in hybridoma cell culture supernatants using antigen inhibition of idiotype-anti-idiotype interaction between as first rodent monoclonal idiotypic antibody and a different second rodent monoclonal anti-idiotypic antibody, comprising:
   (a) coating a solid-phase surface with said first rodent monoclonal idiotypic antibody, wherein said first rodent monoclonal idiotypic antibody, after binding to antigen, will not bind to said second rodent monoclonal anti-idiotypic antibody;
   (b) washing said surface;
   (c) contacting said surface of step (b) with a hybridoma cell culture supernatant suspected to contain said second rodent monoclonal anti-idiotypic antibody;
   (d) washing said surface of step (c);
   (e) contacting the product of step (d) with normal mouse serum;
   (f) washing the surface of the product of step (e);
   (g) contacting the product of step (f) with said first rodent monoclonal idiotypic antibody labeled to provide a detectable signal;
   (h) washing the surface of the product of step (g);
   (i) identifying the presence of said labeled first rodent monoclonal idiotypic antibody in supernatants by the presence of said detectable signal; (j) testing the supernatants identified in step (i) for inhibition by an unpurified antigen, of the interaction between said labeled first rodent monoclonal idiotypic antibody and said second unlabeled rodent monoclonal anti-idiotypic antibody according to the method of claim 20; and (k) selecting hybridomas of the supernatants that show said inhibition for further cloning.

22. The screening method according to claim 21, wherein said antigen is present in step (j) in a mixture of antigens.

23. A method of screening monoclonal antibodies according to claim 21 wherein said label is $^{125}$I.

24. A method of screening monoclonal antibodies according to claim 21 wherein said antigen is Pb44 of *Plasmodium berghei sporozites*.

25. A method of screening monoclonal antibodies according to claim 21 wherein said solid phase surface is the inside surface of the wells of a plastic microtiter plate.

26. A method of screening monoclonal antibodies according to claim 21 wherein said antibody coated on a solid-phase surface specific for an isotype of said second antibody is affinity purified over an immunoabsorbent of said second antibody prior to being coated on said solid-phase surface.

* * * * *